United States Patent [19]

Fisher et al.

[11] Patent Number: 5,030,640

[45] Date of Patent: Jul. 9, 1991

[54] β-ADRENERGIC AGONISTS AND PHARMACEUTICAL COMPOSITIONS THEREOF

[75] Inventors: Michael H. Fisher, Ringoes; Matthew J. Wyvratt, Mountainside, both of N.J.

[73] Assignee: Merck & Co., Inc., Rahway, N.J.

[21] Appl. No.: 293,785

[22] Filed: Jan. 5, 1989

[51] Int. Cl.$^5$ ................... A61K 31/44; C07D 213/73
[52] U.S. Cl. .................................... 514/339; 546/273
[58] Field of Search ...................... 514/339; 546/273

[56] References Cited

U.S. PATENT DOCUMENTS 4,358,455 11/1982 Atkinson ..................... 546/300 X

FOREIGN PATENT DOCUMENTS 244738 11/1987 European Pat. Off. .

Primary Examiner—Robert W. Ramsuer
Assistant Examiner—Jacqueline Haley
Attorney, Agent, or Firm—David L. Rose; Joseph F. Diprima

[57] ABSTRACT

α-Heterocyclic ethanolamino alkylindole derivatives and compositions made therefrom are potent β-agonists having utility as growth promotion agents for animals, bronchodilators, antidepressants and antiobesity agents.

25 Claims, No Drawings

NOVEL β-ADRENERGIC AGONISTS AND PHARMACEUTICAL COMPOSITIONS THEREOF

BACKGROUND OF THE INVENTION

In U.S. Pat. No. 4,358,455 to Atkinson et al. there are disclosed certain aralkyl amino ethanol heterocylic compounds wherein the amino substituent is a phenyl alkyl group optionally substituted with various groups.

In E.P.O. 0,244,728 to Bayer there are disclosed amino alkyl pyridines wherein the amino substituents may be alkyl, cycloalkyl, aralkyl or heterocycle.

SUMMARY OF THE INVENTION

The instant invention concerns certain α-heterocyclic ethanol amino alkyl indoles wherein the indole group is substituted with various lower alkyl, alkoxy or halogen groups which are potent β-agonists. More particularly this invention relates to compounds having the structural formula:

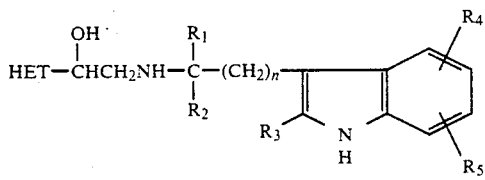

wherein Het, $R_1$, $R_2$, $R_3$, $R_4$, $R_5$ and n are hereinafter defined. This invention also relates to composition having such compounds as the active ingredient for use as growth promotion agents in animals, bronchodilators, antidepressants and antiobesity agents. This invention also relates to processes for the preparation of α-heterocyclic ethanolamino alkyl indoles.

DETAILED DESCRIPTION OF THE INVENTION

The novel compounds of the present invention are represented by the structural formula:

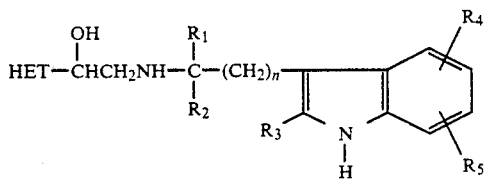

wherein Het is

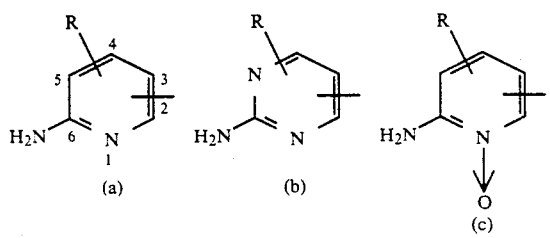

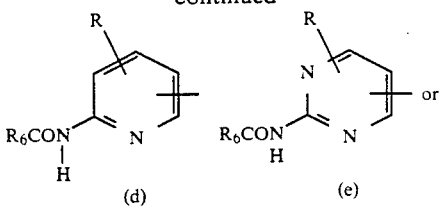

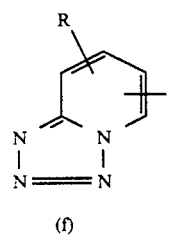

R is hydrogen, halogen or cyano;
$R_6$ is lower alkyl, phenyl, substituted phenyl, phenyl-lower alkyl;
$R_1$ and $R_2$ are independently selected from hydrogen or lower alkyl.
$R_3$ is hydrogen, loweralkyl, phenyl, substituted phenyl, phenyl loweralkyl or substituted phenyl-loweralkyl wherein substituents are 1 to 3 of $R_4$ and $R_5$ which are independently selected from hydrogen, lower alkyl, hydroxy, $OR_7$ or halogen;
$R_7$ is selected from lower alkyl or phenyl-lower alkyl; and n=1–3.

In the instant invention the term "lower alkyl" is intended to include those alkyl groups of either a straight or branched configuration from 1 to 4 carbons exemplified by methyl, ethyl, propyl, isopropyl, butyl, sec-butyl and the like.

The term "halogen" or "halo" is intended to include the halogen atoms of fluorine, chlorine, bromine and iodine.

The preferred compounds of this invention are realized in the above structures wherein:
$R_1$ and $R_2$ are independently selected from hydrogen or lower alkyl;
$R_3$ is hydrogen or loweralkyl;
Het is selected from structures (a), (b), (c), (d) or (e) and the ethanolamine moiety is attached to Het at the 3-position as illustrated in (a).
$R_4$ is hydrogen, halogen, hydroxy or $OR_7$;
$R_5$ is hydrogen;
$R_7$ is lower alkyl;
R is hydrogen or halogen; and n=1 or 2.

Further preferred compounds are realized in the above structures wherein:
Het is structure (a);
$R_1$ and $R_2$ are independently selected from hydrogen or methyl;
$R_3$ is hydrogen, methyl or ethyl;
$R_4$ and $R_5$ are hydrogen and $OR_7$;
$R_7$ is hydrogen or methyl; R is hydrogen and n is 1 or 2.

The optical isomeric forms, that is mixtures of enantiomers or diastereomers, e.g. racemates as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis. For example, the asymmetric center in the ethanolamine chain may be controlled by using a chiral reducing agent such as (R)-alpine borane.

While the carbon atom bearing the hydroxy group of the ethanol amino moiety is always an asymmetric center, a second asymmetric center may be found at the carbon atom bearing the $R_1$ and $R_2$ substituents, depending upon the nature of the $R_1$ and $R_2$ groups.

The stereoisomers formed when the hydroxy group is in the $\beta$-position, that is, above the plane of the ring, are designated R isomers and such R isomers are preferred compounds of this invention since the R isomers have been found to be significantly more active than the S isomers.

Stereoisomers are also formed when $R_1$ and $R_2$ are not identical. In general, the R isomers are preferred over the corresponding S isomers, although in this case, the S isomers still maintain significant activity.

The compounds of this invention when HET is structure (a) are prepared by the following reaction scheme:

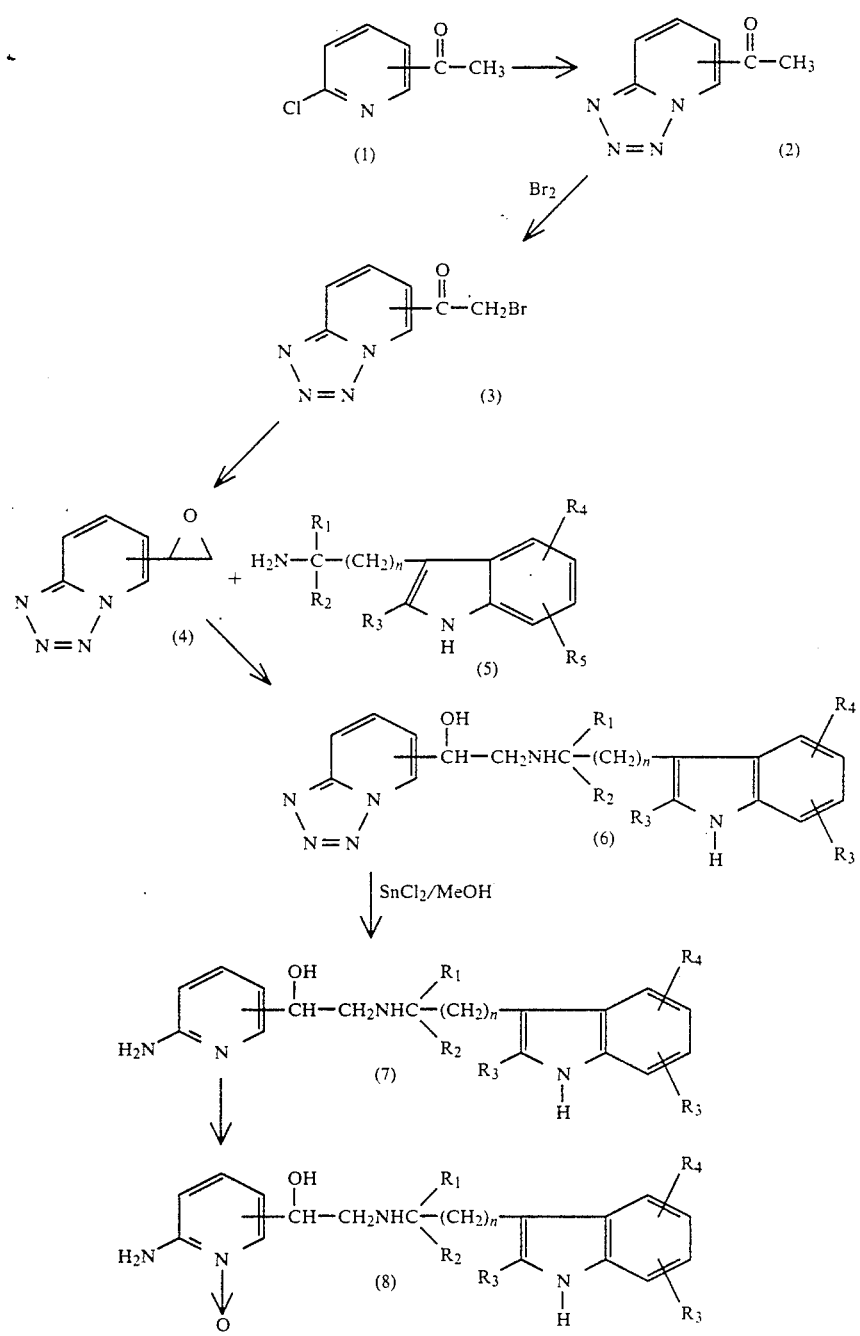

In the foregoing reaction scheme the starting material 2-chloro-acetyl pyridine (1) is treated with sodium azide to prepare the acetyl tetrazolo [1,5-a] pyridine (2). The reaction is carried out in a protic solvent such as an aqueous alcohol in the presence of an acid, preferably hydrochloric acid at from 50° C. to the reflux temperature of the reaction mixture. The reaction is generally complete in from about 5 to 24 hours. This step and the next step are also described in the Atkinson et al. patent.

In the next step the acetyl side chain of compound (2) is brominated with elemental bromine under acidic conditions such as hydrogen bromide or aluminum tribromide in acetic acid to prepare compound (3). The reaction may also be carried out using the analogous chloro reagents to prepare compound (3) with a chloro substituted acetyl group. The reaction is complete in from 1 to 5 hours and is generally carried out at from 0° C. to room temperature. Room temperature is preferred.

Compound (3) may then be converted into the epoxide compound (4) using a mild reducing agent such as sodium borohydride, lithium borohydride and the like. Such reducing agents will produce a racemic mixture of stereoisomers. Optionally a stereospecific reducing agent such as R or S alpine borane may be used which will prepare the optical isomers of the epoxide. The reaction is carried out in an inert solvent from 0° C. to room temperature, preferably at room temperature. The reaction is generally complete in from 1 to 10 days. The progress of the reaction is generally followed by taking aliquots of the reaction mixture and analyzing them for the presence of starting material using, for example, thin layer chromatography. Additional reducing agent may be added as needed. The reaction mixture is then treated with base, such as an alkali metal hydroxide, preferably sodium hydroxide in a protic solvent such as an alcohol or in the presence of a tertiary amine or with excess amine reactant (5). The reaction is generally complete in from ½ to 24 hours at from 0° C. to room temperature, preferably room temperature.

The epoxide is aminated using excess amine in an alcohol solvent heated from 50° C. to reflux. The reaction is generally complete in from 1 to 24 hours. If compound (4) was prepared in a stereospecific manner the optical purity of the product, compound (6) will be preserved. If the amine component contains an asymmetric center (where $R_1$ and $R_2$ are different) a mixture of diastereomers will then be produced. Separation of these diastereomers can be effected by chromatographic procedures or fractional crystallization. Alternatively, an optically pure amine (5) may be used. Compound (6) has the Het group of structure (f).

The tetrazole ring of compound (6) may be removed to prepare the 2-amino pyridine, compound (7), in an alcohol solvent such as methanol with tin (II) chloride. The addition of one equivalent of hydrogen chloride will accelerate the reaction. The reaction is heated at from 50° C. to reflux, preferably for from 1 to 24 hours, affording structure (a) where R is hydrogen.

Compound (7) may be oxidized to produce the pyridine-1-oxide, compound (8), wherein Het is structure (c) and R is hydrogen. The reaction is carried out by protecting the amine and hydroxy groups with an acyl function, preferably a lower alkanoyl group such as acetyl. The acyl protecting groups are prepared using normal acylating techniques such as an acyl anhydride, preferably acetic anhydride. The oxidation is carried out using a mild oxidizing agent such as meta-chloroperbenzoic acid in a chlorinated hydrocarbon, preferably methylene chloride. The reaction is generally complete in from 1 to 4 hours at from 0° C. to room temperature, preferably room temperature. Slightly longer reaction times may be needed however, if larger or bulkier protecting groups are used. The protecting acyl groups are removed using acid or base catalyzed hydrolysis, preferably base catalyzed hydrolysis, following procedures well known to those skilled in the art.

The compounds of this invention are capable of forming salts with various inorganic and organic acids and such salts are also within the scope of this invention. Typical acids are hydrochloric, citric, hydrobromic, sulfuric, phosphoric, methanesulfonic, toluenesulfonic, maleic, fumaric, camphorsulfonic and the like. The non-toxic physiologically acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The compounds of this invention are useful as animal growth promotants, bronchodilators, anti-depressants and antiobesity agents.

The compounds of this invention can be used to increase the growth and feed efficiency of ruminant and non-ruminant animals such as sheep, cattle, goats, horses, swine, chickens and the like. The active compounds can be fed to the animal by incorporating it into the animal's feed or drinking water or it can be administered in a unit dosage form either orally as a drench, tablet, bolus or sustained release bolus or parenterally by injection or from a subcutaneous implant. The administration of the active compounds will produce a surprising increase in body weight, decrease in body fat and increase in body protein for the same food intake.

The active compounds can be administered to the animals at daily rates of from 0.001 to 10 mg/kg of body weight which may vary depending upon the particular animal being treated as well as the age and general physical condition of the animal. Preferably, daily dosages of from 0.01 to 1.0 mg/kg are utilized. When administered as part of the animal's feed or drinking water the active compound is present at rates of from 0.01 to 100 ppm which is determined to provide the appropriate daily amounts of the growth promotant compound.

At the same dosages listed above for growth promotion effects, substantial increases in feed efficiency are also observed.

Compounds of this invention also have bronchodilator activity. The compounds are thus useful to treat conditions in mammals especialy human beings which benefit from bronchodilation such as asthma, etc. For use as a bronchodilator, the compound is administered orally or parenterally in conventional dosage form such as tablet, capsule, solution, dispersion, emulsion and the like. The compound may also be administered as a spray or an aerosol using an appropriate delivery device and formulation. The aerosol route is generally employed. Sufficient compound is administered to produce the desired level of bronchodilation. Daily dosages for oral or parenteral administration may range from about 1 mg to about 300 mg, and preferably from about 2 to about 150 mg. Spray or aerosol delivery will be in metered doses ranging from about 50 to about 1000 mcg, administered as needed.

The instant compounds are also useful for the treatment of clinical depression often characterized by being readily irritable or anxious with crying spells, and a lack of self confidence. The patient may have difficulty concentrating and lose interest in all usual activities including work, social activities and family. Often anorexia, chronic fatigue and either insomnia or hypersomnia may be present. Treatment is often difficult and extends over a prolonged period of time. Chemical antidepressants, such as the compounds of this invention, have been found to be helpful in the management of such depressive conditions.

The compounds of this invention promote lipolysis, the hydrolysis of fat tissue, and thus may be effective in causing weight reductions in obese patients. The compounds, as antiobesity agents, thus assist in maintaining the patient's optimum weight and further avoid the numerous physical complications associated with obesity.

For use as antidepressants and as antiobesity agents, the compounds of the present invention can be administered orally, by inhalation, by suppository or parenterally, i.e., intravenously, intraperitoneally, etc. and in any suitable dosage form. The compounds may be offered in a form (1) for oral administration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitble liquid carrier—or in capsules or encapsulated in suitable encapsulating material, or (2) for parentered administration, dissolved, dispersed, or emulsified in a suitable liquid carrier or diluent or (3) as an aerosol or (4) as a suppository. The ratio of active ingredient (present compound) to compounding ingredients will vary as the dosage form requires. Conventional procedures are used to prepare the pharmaceutical formulations. The effective daily dosage level for the present compounds may be varied from about 10 mg to about 3000 mg. Daily doses ranging from about 100 to about 2500 mg are preferred, with about 200 to about 1000 mg being a more preferred range. Oral administration is preferred. Either single or multiple daily doses may be administered depending on unit dosage.

EXAMPLE 1

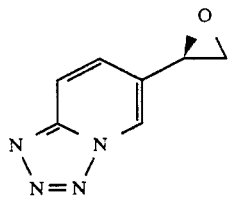

(R)-2-(tetrazolo[1,5-a]pyrid-6-yl)oxirane

In a 12-liter 3-necked flask under nitrogen, 304 g (1.26 mol) of 6-bromoacetyltetrazolo[1,5-a]pyridine was cooled with an ice-bath. By means of a large bore canulla, 4.8 liters (2.4 mol) of commercial 0.5M (R)-Alpine Borane in tetrahydrofuran (Aldrich) was slowly added to the 6-bromoacetyltetrazolo[1,5-a]pyridine mixture. A nitrogen inlet tube was submerged into the reaction solution and the reaction mixture permitted to warm to 30° C. (warm water bath). Nitrogen was passed through the solution until the reaction solution was approximately one-third its original volume. The dark red solution was permitted to stir at room temperature for 3 days. TLC (silcia gel) of the reaction mixture indicated that starting material remained. An additional 200 ml of 0.5M (R)-Alpine Borane was added and concentrated as above to its original volume. The reaction mixture was stirred an additional two days at room temperature. The reaction mixture was then added to 10 liters of a cold aqueous solution of sodium hydroxide (2.5N) with vigorous stirring. To this mixture, 8 liters of methylene chloride was added and the layers separated. The aqueous layer was further extracted with methylene chloride and the combined organic layers backwashed with 2.5N NaOH, water and brine. The methylene chloride solution was dried with anhydrous sodium sulfate and filtered through a silica gel plug. The filtrate was concentrated under reduced pressure. The residue was then chromatographed on a silica gel (5 Kg) column. The column was eluted first with methylene chloride and then with ethyl acetate:hexane (2:3 to 3:2). Concentration of the appropriate fractions gave 121 g of pure (R)-epoxide; IR (Nujol)=1640, 1510, 1245, 1200, 1150, 1095, and 830 cm$^{-1}$; $[\alpha]_D^{25}=+6.5$ (c=1, acetone). Optical purity was checked by reaction with (R)-$\alpha$-methyl benzylamine. Examination of the crude product by $^1$H NMR revealed only 3% of the (S)-epoxide isomer.

EXAMPLE 2

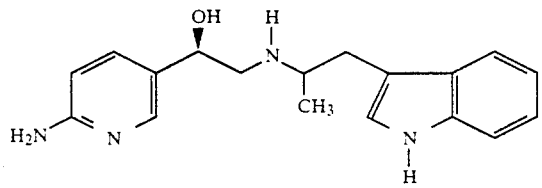

(R)-6-Amino-$\alpha$-[[(1-methyl-2-(1H-indol-3-yl)ethyl)amino]methyl]-3-pyridinemethanol Citrate A solution of 650 mg (4.0 mmol) of (R)-2-(tetrazolo[1,5-a]pyrid-6-yl)oxirane and 597 mg (3.43 mmol) of $\alpha$-methyltryptamine in 12 ml of absolute ethanol was heated at reflux for two hours under nitrogen. The reaction mixture was concentrated under reduced pressure and the residue (1.4 g) chromatographed on silica gel (92:8:1 CH$_2$Cl$_2$:MeOH:conc. NH$_4$OH) to give 0.86 g of product (R$_f$=0.32). This material was dissolved in absolute ethanol and treated with ethanolic hydrochloric acid. Trituration with ethyl acetate and concentration afforded 1.01 g of (R)-[[(1-methyl-2-(1H-indol-3-yl)ethyl)amino]methyl]tetrazolo[1,5-a]pyridine-6-methanol dihydrochloride; $[\alpha]_D^{25}=-21.4$ (MeOH).

A solution of 1.01 g of this material in 25 ml of methanol was treated with 1.13 g (5 mmol) of SnCl$_2$.2H$_2$O. The reaction mixture was heated at reflux for 5 hours and then concentrated to about half its original volume. To this concentrated solution 30 ml of methylene chloride and 25 ml of 2N NaOH solution were added. The layers were separated and the aqueous phase further extracted with methylene chloride. The combined organic layers were washed with saturated sodium chloride solution, dried and concentrated to dryness. The residue (596 mg) was chromatographed on silica gel (85:15:1.5 CH$_2$Cl$_2$:MeOH:conc. NH$_4$OH) to give 475 mg of product (R$_f$=0.29).

A solution of the aminopyridine product (400 mg, 1.29 mmol) in 10 ml of absolute ethanol was added dropwise to a stirred solution of citric acid (250 mg, 1.30 mmol) in 6 ml of ethanol. The mixture was slurried for an hour and then filtered. The precipitate was rinsed with ethanol and ether to afford 621 mg of salt, mp 137°–143° C.

EXAMPLE 3

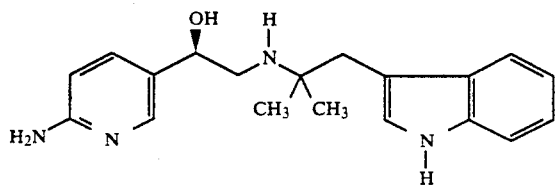

(R)-6-Amino-α-[[(1,1-dimethyl-2-(1H-indol-3-yl)ethyl)amino]methyl]-3-pyridinemethanol Dihydrochloride A solution of 670 mg (3.58 mmol) of (1,1-dimethyl-2-(1H-indol-3-yl)ethyl amine (B. Heath-Brown and P. G. Philpott, J. Chem. Soc., 7165 (1965)) and 598 mg (3.69 mmol) of (R)-2-(tetrazolo[1,5-a]pyrid-6-yl)oxirane in 12 ml of absolute ethanol was heated at reflux for 15 hours. The reaction mixture was concentrated and the residue (1.24 g) chromatographed on silica gel (95:5:1 $CH_2Cl_2$:MeOH:conc. $NH_4OH$) to give 808 mg of (R)-α-[[(1,1-dimethyl-2-(1H-indol-3-yl)ethyl)amino]methyl]tetrazolo[1,5-a]pyridine-6-methanol.

This material (775 mg, 2.21 mmol) was dissolved in 22 ml of methanol and treated with 0.21 ml of concentrated HCl solution and 0.98 g of $SnCl_2.2H_2O$. The reaction mixture was heated at reflux overnight. The mixture was concentrated and the residue partitioned between 20% MeOH/$CH_2Cl_2$ (30 ml) and 2N NaOH (25 ml). The layers were separated and the aqueous phase further extracted with 20% MeOH/$CH_2Cl_2$. The organic extracts were washed with saturated sodium chloride solution and dried with anhydrous magnesium sulfate. The solution was concentrated and the residue chromatographed on silica gel (90:10:1 $CH_2Cl_2$:MeOH:$NH_4OH$) to give 589 mg of product.

A solution of 343 mg of this product in 10 ml of absolute ethanol was treated with an ethanolic solution of HCl in excess. A precipitate formed upon the addition of ether. This material was collected and rinsed with cold ethanol and ether to give 405 mg of salt; mp 256°–258° C. (dec); $[\alpha]_D^{25°} = -32.2$ (c=1.0, MeOH); Analysis: Calculated for $C_{19}H_{26}N_4OCl_2.0.5H_2O$:

C, 56.15; H, 6.70; N, 13.79; Cl, 17.45. Found: C, 56.26; H, 6.69; N, 13.64; Cl, 16.85.

EXAMPLE 4

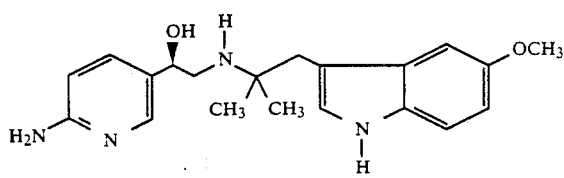

(R)-6-Amino-α-[[(1,1-dimethyl-2-(5-methoxy-1H-indol-3-yl)ethyl)amino]methyl]-3-pyridinemethanol Dihydrochloride A solution of 598 mg of (R)-2-(tetrazolo[1,5-a]pyrid-6-yl)oxirane and 782 mg of (1,1-dimethyl-2-(5-methoxy-1H-indol-3-yl)ethyl amine (B. Heath-Brown and P. G. Philpott, J. Chem. Soc., 7165 (1965)) in 12 ml of absolute ethanol was heated at reflux for 44 hours. The reaction mixture was concentrated and the residue (1.15 g) was chromatographed on silica gel (95:5:0.5 $CH_2Cl_2$:MeOH:$NH_4OH$) to give 0.997 g of (R)-α-[[(1,1-dimethyl-2-(5-methoxy-1H-indol-3-yl)ethyl)amino]methyl]tetrazolo[1,5-a]pyridine-6-methanol.

To a solution of this product (0.997 g) in 27 ml of methanol, 0.26 ml of concentrated HCl and 1.209 g of $SnCl_2.2H_2O$ were added and the reaction mixture heated under nitrogen for 16 hours. This mixture was then poured into a two phase mixture of 162 ml of 1N NaOH and 110 ml of $CH_2Cl_2$ and stirred for one hour. The layers were separated and the aqueous layer further extracted with $CH_2Cl_2$. The combined organic layers were washed with saturated sodium chloride solution and dried with anhydrous magnesium sulfate. The solution was concentrated to give product (0.793 g). Spectroscopic evidence ($^1H$ NMR and mass spectrum) is consistent with the structure. The product was dissolved in a minimum amount of absolute ethanol and excess ethanolic HCl was added. Ether was added to facilate precipitation of the salt which was then collected by filtration to give 820 mg of product; $[\alpha]_D$ 25° = −31.4 (c=1.0, MeOH);

Analysis: Calculated for $C_{20}H_{26}N_4O_2.2HCl$: C, 56.21; H, 6.60; N, 13.11; Cl, 16.59. Found: C, 56.58; H, 6.92; N, 13.48; Cl, 16.31.

EXAMPLE 5

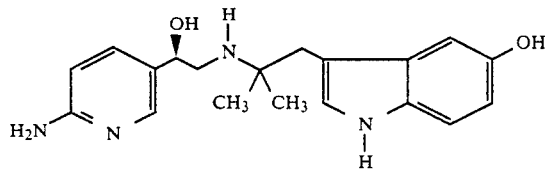

(R)-6-Amino-α-[[(1,1-dimethyl-2-(5-hydroxy-1H-indol-3-yl))ethyl)amino]methyl]-3-pyridinemethanol Dihydrochloride A solution of 725 mg (3.55 mmol) of (1,1-dimethyl-2-(5-hydroxy-1H-indol-3-yl))ethyl amine (R. V. Heinzelman, et al., J. Org. Chem., 25, 1548 (1960)) and 598 mg of (R)-2-(tetrazolo[1,5-a]pyrid-6-yl)oxirane in 15 ml of absolute ethanol was stirred at reflux under nitrogen for 13 hours. The reaction mixture was concentrated under reduced pressure to give 1.05 g of crude product. This material was chromatographed on silica gel (90:10:1 $CH_2Cl_2$:MeOH:$NH_4OH$) to give 927 mg of partially purified material. Preparative TLC on silica gel in the same solvent system (eluted twice) afforded pure (R)-α-[[(1,1-dimethyl-2-(5-hydroxy-1H-indol-3-yl))ethyl)amino]methyl]tetrazolo[1,5-a]pyridine-6-methanol (741 mg).

This tetrazole product (741 mg) was dissolved in 20 ml of methanol and treated with 0.19 ml of concentrated HCl and 900 mg of $SnCl_2.2H_2O$. The reaction mixture was heated at reflux under nitrogen for 15 hours. The mixture was cooled and H₂S was bubbled into the solution. The resulting precipitate was collected by filtration and the filtrate concentrated under reduced pressure. The crude product was purified by preparative TLC on silica gel (85:15:0.5 CH₂Cl₂:MeOH:NH₄OH) to give 185 mg of pure product. This material was dissolved in absolute ethanol and treated with excess ethanolic HCl. Treatment with ether gave the hydroscopic salt which was collected by filtration, 169 mg. Analysis: Calculated for C₁₉H₂₄N₄O₂.2HCl: C, 55.21; H, 6.34; N, 13.55; Cl, 17.15. Found: C, 54.63; H, 6.43; N, 12.65; Cl, 16.82.

EXAMPLE 6

EXAMPLE 6

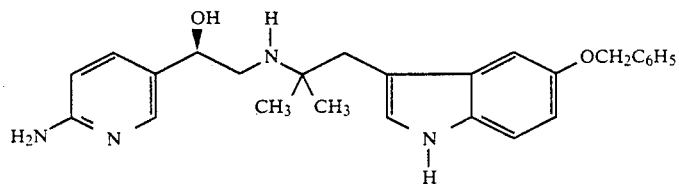

(R)-6-Amino-α-[[(1,1-dimethyl-2-(5-benzyloxy-1H-indol-3-yl))ethyl)amino]methyl]-3-pyridinemethanol Dihydrochloride A solution of (R)-2-(tetrazolo[1,5-a]pyrid-6-yl)oxirane (0.60 g) and (1,1-dimethyl-2-(5-benzyloxy-1H-indol-3-yl))ethyl amine (1.09 g, 3.55 mmol) in 15 ml of absolute ethanol was heated at reflux for 23 hours under an inert atmosphere. The reaction mixture was concentrated under reduced pressure to give crude product (1.59 g) which was chromatographed on silica gel (95:5:0.5 CH₂Cl₂:MeOH:NH₄OH) to give 1.27 g of (R)-α-[[(1,1-dimethyl-2-(5-benzyloxy-1H-indol-3-yl))ethyl)amino]methyl]tetrazolo[1,5-a]pyridine-6-methanol.

To a solution of this product (1.13 g) in 25 ml of methanol, 0.23 ml of concentrated HCl and 1.1 g of SnCl₂.2H₂O were added. The resulting mixture was heated at reflux for 16 hours under nitrogen. The reaction mixture was then poured into a mixture of 100 ml of CH₂Cl₂ and 144 ml of 1N NaOH. The layers were separated and the aqueous phase further extracted with CH₂Cl₂. The combined organic phases were backwashed with saturated sodium chloride solution and dried with anhydrous magnesium sulfate. The solution was flash chromatographed on silica gel (90:10:1 CH₂Cl₂:MeOH:NH₄OH) to give 855 mg of product. An ethanolic solution of this material was treated with HCl/EtOH and then triturated with ether. The hydrochloride salt was collected by filtration, 894 mg; $[\alpha]_D$ 25° = −26.6 (c=1.5, MeOH). Analysis: Calculated for C₂₆H₂₈N₄O₂.2HCl: C, 62.28; H, 6.03; N, 11.17; Cl, 14.14. Found: C, 62.29; H, 6.35; N, 11.35; Cl, 14.45.

EXAMPLE 7

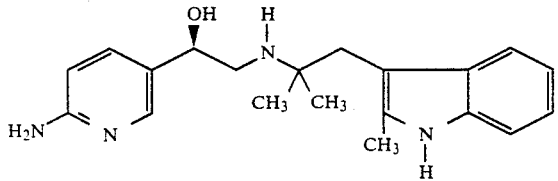

(R)-6-Amino-α-[[(1,1-dimethyl-2-(2-methyl-1H-indol-3-yl))ethyl)amino]methyl]-3-pyridinemethanol Maleate A mixture of 1.08 g of 2-methylgramine, 0.28 g of NaOH and 3.7 ml of 2-nitropropane were stirred and heated at reflux for 18 hours under nitrogen. The reaction mixture was then treated with 5 ml of 10% HOAc and stirred at room temperature for two hours. The mixture was diluted with water and repeatedly extracted with ether. The combined etheral extracts were backwashed with saturated sodium chloride solution and dried with anhydrous magnesium sulfate. Concentration afforded a residue (1.42 g) which was chromatographed on silica gel (1:1 CH₂Cl₂:hexane) to give pure product, 1.61 g, mp 102°–104° C.

NiCl₂.6H₂O (768 mg) was suspended in 60 ml of methanol and sonicated in order to dissolve the nickel salt. NaBH₄ (367 mg) was added in small portions and then sonicated for 30 minutes. The above nitro compound (1.5 g) was added and the reaction mixture sonicated. Additional NaBH₄ (854 mg) was added in small portions over time. After two hours the reaction mixture was filtered and the filtrate concentrated to dryness under reduced pressure. The residue was chromatographed on silica gel (90:10:1 CH₂Cl₂:MeOH:NH₄OH) to give 934 mg of amine.

A solution of this amine (907 mg) and (R)-2-(tetrazolo[1,5-a]pyrid-6-yl)oxirane (745 mg) in 20 ml of methanol was heated at reflux for 39 hours. The reaction mixture was concentrated to dryness and chromatographed on silica gel (95:5:1 CH₂Cl₂:MeOH:NH₄OH) to give 1.27 g of (R)-α-[[(1,1-dimethyl-2-(2-methyl-1H-indol-3-yl))ethyl)amino]methyl]tetrazolo[1,5-a]pyridine-6-methanol.

To a solution of this material (1.27 g) in 33 ml of methanol, 0.33 ml of concentrated HCl and 1.55 g of SnCl₂.2H₂O were added. The resulting mixture was heated at reflux for 16 hours and then poured into a mixture of CH₂Cl₂ (100 ml) and 1N NaOH (200 ml). The layers were separated and the aqueous layer further extracted with CH₂Cl₂. The combined organic extracts were backwashed with saturated sodium chloride solution and dried with anhydrous magnesium sulfate. Concentration afforded 955 mg of product. This material (208 mg) and maleic acid (142 mg) were dissolved in ethanol. After 10 minutes this solution was poured into ether. The resulting maleate salt was collected and dried, 228 mg; $[\alpha]_D$ 25° = −16.8 (c=0.16 in MeOH). Analysis: Calculated for C₂₈H₃₄N₄O₉.0.5C₂H₅OH: C, 58.66; H, 6.28; N, 9.44. Found: C, 59.03; H, 6.41; N, 9.58.

EXAMPLE 8

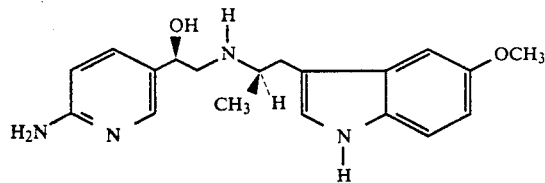

(R)-6-Amino-α-[[(1(R)-methyl-2-(5-methoxy-1H-indol-3-yl)ethyl)amino]methyl]-3-pyridinemethanol Didhydrochloride A solution of 553 mg of partially resolved (R)-1-methyl-2-(5-methoxy-1H-indol-3-yl)ethyl amine (R. A. Glennor et al, Biol Psychiatry, 18,493 (1983) and 452 mg of (R)-2-(tetrazolo[1,5-a]pyrid-6-yl)oxirane in 10 ml of methanol under nitrogen was heated at reflux for 24 hours. The reaction mixture was concentrated under reduced pressure and the residue (1.0 g) purified by careful preparative TLC on silica gel (95:5:0.5 CH$_2$Cl$_2$:MeOH:NH$_4$OH) to give 515 mg of (R)-α-[[(1(R)-methyl-2-(5-methoxy-1H-indol-3-yl)ethyl)amino]methyl]tetrazolo[1,5-a]pyridine-6-methanol plus 11.6 mg of the adduct resulting from the small amount of (S)-amine present in the starting material.

To a solution of the (R)-α-[[(1(R)-methyl-2-(5-methoxy-1H-indol-3-yl)ethyl)amino]methyl]tetrazolo[1,5-a]pyridine-6-methanol (509 mg) in 14 ml of methanol, 0.13 ml of concentrated HCl and 616 mg of SnCl$_2$.2H$_2$O were added and the mixture heated at reflux under nitrogen for 16 hours. The reaction mixture was poured into a mixture of CH$_2$Cl$_2$ (55 ml) and 1N NaOH (83 ml) and stirred for 30 minutes. The layers were separated and the aqueous layer repeatedly extracted with CH$_2$Cl$_2$. The combined organic extracts were washed with saturated sodium chloride solution and dried with anhydrous magnesium sulfate. The solution was concentrated to dryness. The residue (343 mg) was purified by preparative TLC on silica gel (90:10:1 CH$_2$Cl$_2$:MeOH:NH$_4$OH) to give 179 mg of product. This material was dissolved in a minimum amount of ethanol and made acidic with ethanolic HCl. The solution was then triturated with ether and the precipitate collected by filtration to give 202 mg of salt; $[\alpha]_D$ 25° = −45.9 (c=0.85, MeOH); Analysis: Calculated for C$_{19}$H$_{24}$N$_4$O$_2$.2HCl:C, 55.21; H, 6.34; N, 13.56; Cl, 17.15. Found: C, 55.69; H, 6.81; N, 13.24; Cl, 16.69.

EXAMPLE 9

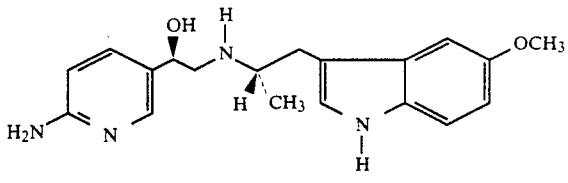

(R)-6-Amino-α-[[(1(S)-methyl-2-(5-methoxy-1H-indol-3-yl)ethyl)amino]methyl]-3-pyridinemethanol dihydrochloride A solution of 350 mg of (R)-2-(tetrazolo[1,5-a]pyrid-6-yl)oxirane and 429 mg of (S)-1-methyl-2-(5-methoxy-1H-indol-3-yl)ethyl amine (R. A. Glennon et al., Biol. Psychiatry, 18, 493 (1983) in 8 ml of methanol was heated at reflux under nitrogen for 20 hours. The reaction mixture was concentrated under reduced pressure and the residue (765 mg) was purified twice by preparative TLC on silica gel (95:5:0.5 CH$_2$Cl$_2$:MeOH:NH$_4$OH) to give 419 mg of (R)-α-[[(1(S)-methyl-2-(5-methoxy-1H-indol-3-yl)ethyl)amino]methyl]tetrazolo[1,5-a]pyridine-6-methanol.

To a solution of this tetrazole (391 mg) in 10 ml of methanol, 0.1 ml of concentrated HCl and 473 mg of SnCl$_2$.2H$_2$O were added. The reaction mixture was heated at reflux under nitrogen for 16 hours and then poured into a solution of CH$_2$Cl$_2$ (45 ml) and 1N NaOH solution (64 ml). The mixture was stirred for 20 minutes and the layers then separated. The aqueous phase was further extracted with CH$_2$Cl$_2$. The combined organic extracts were backed washed with saturated sodium chloride solution and dried with anhydrous magnesium sulfate. The solution was concentrated and the crude residue (309 mg) was purified by preparative TLC on silica gel (90:10:1 CH$_2$Cl$_2$:MeOH:NH$_4$OH) to afford pure product which was converted to its hydrochloride salt with ethanolic HCl. The salt was isolated by dilution with ether and filtration, 240 mg; mp 264° C.; $[\alpha]_D$ 25° = −8.45 (c=1.0, MeOH); Analysis: Calculated for C$_{19}$H$_{24}$N$_4$O$_2$.2HCl: C, 55.21; H, 6.34; N, 13.56. Found: C, 54.82; H, 6.60; N, 13.08.

EXAMPLE 10

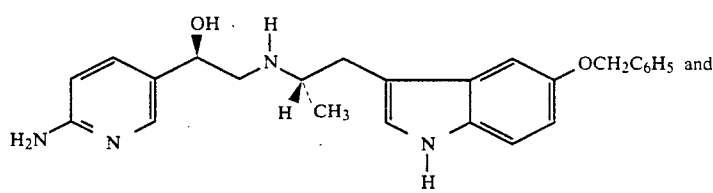
and
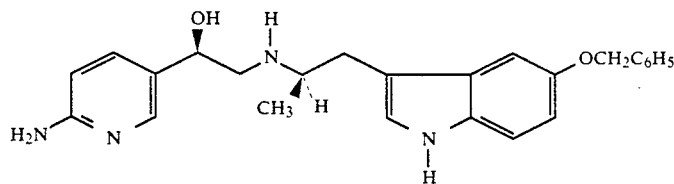

(R)-6-Amino-α-[[(1(R)-methyl-2-(5-benzyloxy-1H-indol-3-yl)ethyl)amino]methyl]-3-pyridinemethanol and
(R)-6-Amino-α-[[(1(S)-methyl-2-(5-benzyloxy-1H-indol-3-yl)ethyl)amino]methyl]-3-pyridinemethanol A solution of 3.24 g of (R)-2-(tetrazolo-[1,5-a]pyrid-6-yl)oxirane and 5.89 g of 1-methyl-2-(5-benzyloxy-1H-indol-3-yl)ethyl amine in 84 ml of absolute ethanol was heated at reflux under nitrogen for 24 hours. The reaction mixture was concentrated and the residue purified by preparative TLC on silica gel (95:5:0.5 CH₂Cl₂:MeOH:NH₄OH) to give 1.29 g of (R)-α-[[(1(R)-methyl-2-(5-benzyloxy-1H-indol-3-yl)ethyl)amino]methyl]tetrazolo[1,5-a]pyridine-6-methanol and 1.46 g of (R)-α-[[(1(S)-methyl-2-(5-benzyloxy-1H-indol-3-yl)ethyl)-amino]methyl]tetrazolo[1,5-a]pyridine-6-methanol.

To a solution of the (R,R) tetrazole (1.28 g) in 29 ml of methanol, 0.28 ml of concentrated HCl and 1.33 g of SnCl₂·2H₂O were added and the mixture heated at reflux under nitrogen for 17 hours. The reaction mixture was poured into a solution of CH₂Cl₂ (120 ml) and 1N NaOH (174 ml) and stirred for 15 minutes. The layers were separated and the aqueous phase further extracted with CH₂Cl₂. The combined organic phases were backwashed with saturated sodium chloride solution and dried with anhydrous magnesium sulfate. The solution was concentrated and the residue purified by preparative TLC on silica gel (90:10:1 CH₂Cl₂:MeOH:NH₄OH) to give 814 mg of (R)-6-Amino-α-[[(1(R)-methyl-2-(5-benzyloxy-1H-indol-3-yl)ethyl)amino]methyl]-3-pyridinemethanol.

To a solution of the (R,S)-diastereomer (1.4 g) in 32 ml of methanol, 0.31 ml of concentrated HCl and 1.46 g of SnCl₂·2H₂O were added and the reaction mixture heated at reflux for 17 hours. The mixture was then taken to dryness under reduced pressure and the residue (1.66 g) purified by preparative TLC on silica gel (90:10:1 CH₂Cl₂:MeOH:NH₄OH) to give 644 mg of (R)-6-Amino-α-[[(1(S)-methyl-2-(5-benzyoxy-1H-indol-3-yl)ethyl)amino]methyl]-3-pyridinemethanol.

EXAMPLE 11

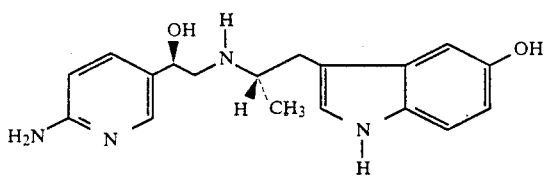

(R)-6-Amino-α-[[(1(S)-methyl-2-(5-hydroxy-1H-indol-3-yl)ethyl)amino]methyl]-3-pyridinemethanol Dihydrochloride A solution of (R)-6-Amino-α-[[(1(S)-methyl-2-(5-benzyloxy-1H-indol-3-yl)ethyl)amino]methyl]-3-pyridinemethanol (619 mg) in 47 ml of absolute ethanol containing 7.9 g of cyclohexene and 198 mg of 10% Pd/C was heated at reflux under nitrogen for 3 hours. The reaction mixture was filtered and concentrated to dryness (510 mg). This residue was purified twice by preparative TLC (85:15:0.5 CH₂Cl₂:MeOH:NH₄OH) to give 224 mg of (R)-6-Amino-α-[[(1(S)-methyl-2-(5-hydroxy-1H-indol-3-yl)ethyl)amino]methyl]-3-pyridinemethanol.

An ethanolic solution of this product (202 mg) was treated with a saturated solution of HCl in ethanol until acidic. The salt was precipitated with ether and collected by filtration, 219 mg. This material was dissolved in warm isopropanol, filtered and then treated with ether to re-precipitate the salt, 140 mg; [α]_D 25 = −40.0 (c=1.0, MeOH).

EXAMPLE 12

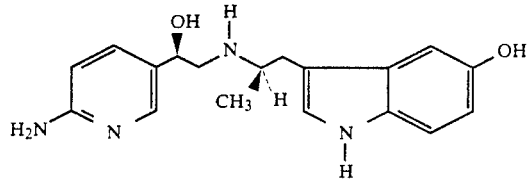

(R)-6-Amino-α-[[(1(R)-methyl-2-(5-hydroxy-1H-indol-3-yl)ethyl)amino]methyl]-3-pyridinemethanol Dihydrochloride To a solution of 800 mg of (R)-α-[[(1(R)-methyl-2-(5-benzyloxy-1H-indol-3-yl)ethyl)amino]methyl]tetrazolo[1,5-a]pyridine-6-methanol in 60 ml of ethanol, 9.1 ml of cyclohexene and 328 mg of 10% Pd/C were added under nitrogen. The reaction mixture was stirred at reflux for 3 hours, cooled and then filtered. The filtrate was concentrated under reduced pressure and the residue (659 mg) was purified by preparative TLC on silica gel (85:15:0.5 CH₂Cl₂:MeOH:NH₄OH) to give 187 mg of product. This material was dissolved in ethanol and treated with excess ethanolic HCl until the amine solution was acidic. The solution was concentrated and the residue dissolved in isopropanol. Treatment with ether afforded the hydrochloride salt, 144 mg;—[α]_D 25° = −36.6 (MeOH).

EXAMPLE 13

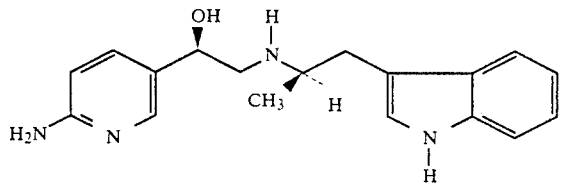

(R)-6-Amino-α-[[(1(R)-methyl-2-(1H-indol-3-yl)ethyl)amino]methyl]-3-pyridinemethanol Citrate A solution of 325 mg of (R)-2-(tetrazolo[1,5-a]pyrid-6-yl)oxirane and 300 mg of (R)-α-methyltryptamine in 6 ml of absolute ethanol is heated at reflux under nitrogen for two hours. The reaction mixture is concentrated and the residue purified by silica gel chromatography to give (R)-α-[[(1(R)-methyl-2-(1H-indol-3-yl)ethyl)amino]-methyl]tetrazolo[1,5-a]pyridine-6-methanol.

A solution of 0.5 g of this tetrazole in 15 ml of methanol is treated with 0.6 g of SnCl₂·2H₂O for 5 hours at reflux under nitrogen. The reaction mixture is partially concentrated and then poured into a mixture of 25 ml of CH₂Cl₂ and 15 ml of 1N NaOH solution. The layers are separated and the aqueous layer further extracted with CH₂Cl₂. The combined organic phases are backwashed with saturated sodium chloride solution and dried with anhydrous magnesium sulfate. Concentration of this solution and chromatography on silica gel affords the product which is dissolved in ethanol and treated with one equivalent of an ethanolic solution of citric acid.

The mixture is aged for approximately one hour and the citrate salt is collected by filtration.

EXAMPLE 14

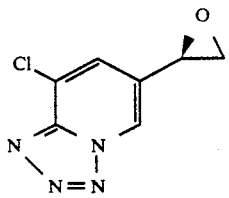

(R)-2-(4-Chloro-tetrazolo[1,5-a]pyrid-6-yl)oxirane

To a cold (0° C.), stirred slurry of 19.4 g of 5,6-dichloronicotinic acid in 300 ml of anhydrous ether under nitrogen, an etheral solution of methyllithium (1.4M, 150 ml) was added dropwise over 1.5 hours. After twenty minutes an additional 40 ml of 1.4M methyllithium was slowly added. The reaction mixture was stirred for 30 minutes and then slowly quenched into 500 g of ice-water. The mixture was extracted with ether (2×200 ml) and dried with anhydrous magnesium sulfate. Concentration afforded 7.83 g of crude product which was chromatographed on silica gel (1:3 ethyl acetate:hexanes) to give 3.68 g of product ketone, mp. 77°-82° C.

A solution of 1.0 g of ketone and 684 mg of sodium azide in 5 ml of ethanol containing 0.66 ml of concentrated HCl and 5 ml of water was heated at reflux under nitrogen overnight. The reaction mixture was cooled and 310 mg of $Na_2CO_3$ in 5 ml of water was added. The precipitate was collected (960 mg) and the filtrate further extracted with $CH_2Cl_2$. The combined extracts were dried with sodium sulfate and concentrated to give an additional 180 mg of tetrazole.

To a stirred solution of 840 mg of tetrazole in 12 ml of glacial acetic acid under nitrogen, 0.22 ml of bromine was added followed by slow addition of 1.07 ml of a 1.0M solution of $AlBr_3$ in dibromomethane. The reaction mixture was stirred for 5 minutes and then 0.25 ml of methanol was added and the mixture stirred overnight. The solution was then poured into ice-water and the solution extracted with $CH_2Cl_2$. The combined extracts were backwashed with saturated sodium bicarbonate solution and saturated sodium chloride solution and then dried with anhydrous sodium sulfate. Concentration afforded 988 mg of α-bromoketone.

To a cold (0° C.), stirred solution of this bromoketone (1.0 g) in 55 ml of tetrahydrofuran (THF), 14.5 ml of 0.5M (R)-alpine borane in THF was added dropwise under nitrogen. The reaction mixture was stirred at room temperature for 13 days. An additional 8 ml of (R)-alpine borane was added and the solution stirred three more days. The reaction mixture was concentrated under reduced pressure and redissolved in 30 ml of $CH_2Cl_2$. To this solution 35 ml of 2.5N NaOH solution was added and the resulting mixture vigorously stirred for 2 hours. The layers were separated and the aqueous phase further extracted with $CH_2Cl_2$. The combined extracts were washed with saturated sodium chloride solution and dried ($Na_2SO_4$). Concentration and chromatography on silica gel (1:1 ethyl acetate:hexanes) gave 0.364 g of the (R)-epoxide. The optical purity of the epoxide was determined to be 84% ee by spectroscopic ($^1H$ NMR) evaluation of its adducts with (+)-R-α-methylbenzylamine and dl-α-methylbenzylamine.

EXAMPLE 15

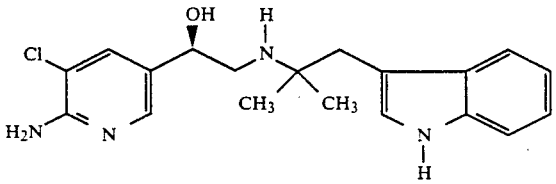

(R)-6-Amino-5-chloro-α-[[(1,1-dimethyl-2-(1H-indol-3-yl)ethyl)amino]methyl]-3-pyridinemethanol Dihydrochloride A solution of 600 mg of (R)-2-(4-chlorotetrazolo[1,5-a]pyrid-6-yl)oxirane and 650 mg of (1,1-dimethyl-2-(1H-indol-3-yl))ethyl amine in 10 ml of absolute ethanol is heated at reflux for 12 hours and then concentrated to dryness under reduced pressure. The residue is chromatographed on silica gel to give (R)-α-[[(1,1-dimethyl-2-(1H-indol-3-yl)ethyl)amino]methyl]tetrazolo[1,5-a]pyridine-4-chloro-6-methanol.

This tetrazole (760 mg) is dissolved in 25 ml of methanol and treated with 0.2 ml of concentrated HCl and 1.0 g of $SnCl_2.2H_2O$. The mixture is heated at reflux for 15 hours and then concentrated under reduced pressure. The residue is partitioned between $CH_2Cl_2$ and 2N NaOH. The layers are separated and the aqueous phase further extracted with $CH_2Cl_2$. The combined extracts are backwashed with saturated sodium chloride solution and dried with anhydrous magnesium sulfate. The solution is concentrated and the residue chromatographed on silica gel to give the aminopyridine product which is converted into its hydrochloride salt with ethanolic HCl.

EXAMPLE 16

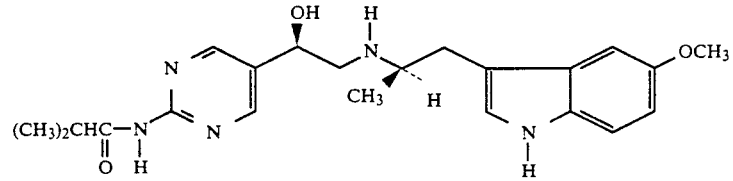

(R)-2-Isobutyramido-α-[[(1(R)-methyl-2-(5-methoxy-1H-indol-3-yl)ethyl)amino]methyl]-5-pyrimidinemethanol A solution of 2-isobutyramido-5-(bromoacetyl)-pyrimidine (1.0 g) and ((R)-1-methyl-2-(5-methoxy-1H-indol-3-yl))ethyl amine (2.5 g) in 100 ml of dry acetonitrile is stirred at room temperature for 30 minutes. The reaction mixture is made acidic with hydrochloric acid and then diluted with ether. The solution is concentrated and redissolved in methanol. To this cooled solution (0° C.), sodium borohydride (0.75 g) is slowly added and the mixture then stirred for one hour. The pH of the solution is adjusted with acetic acid to approximately 6. This solution is extracted with CH₂Cl₂ and the combined extracts backwashed with saturated sodium chloride solution and dried with magnesium sulfate. Concentration and chromatography on silica gel afforded the titled compound. The desired R,R-isomer can be isolated either by fractional crystallization or by careful HPLC chromatography.

EXAMPLE 17

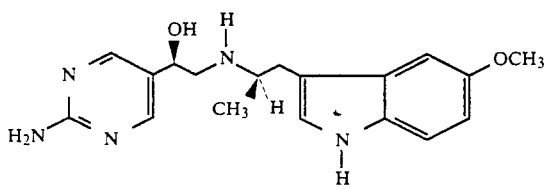

(R)-2-Amino-α-[[(1(R)-methyl-2-(5-methoxy-1H-indol-3-yl)ethyl)amino]methyl]-5-pyrimidinemethanol Dihydrochloride To a solution of 0.5 g of (R)-2-isobutyramido-α-[[(1(R)-methyl-2-(5-methoxy-1H-indol-3-yl)ethyl)amino]methyl]-3-pyrimidinemethanol in 15 ml of ethanol, 0.7 g of potassium hydroxide in 5 ml of methanol is added. The reaction mixture is heated at 70° C. for 2 hours and then partially concentrated under reduced pressure. The concentrated solution is diluted with water and repeatedly extracted with CH₂Cl₂. The combined organic extracts are backwashed with saturated sodium chloride and dried with magnesium sulfate. The solution is concentrated and the residue chromatographed on silica gel to give the desired product which is converted into its hydrochloride salt.

EXAMPLE 18

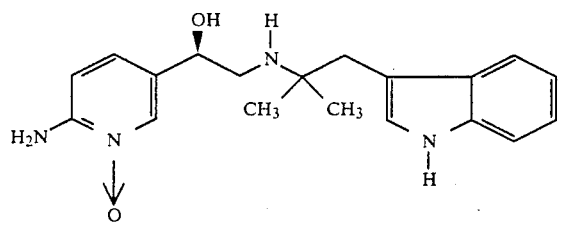

(R)-6-Amino-α-[[(1,1-dimethyl-2-(1H-indol-3-yl)ethyl)amino]methyl]-3-pyridinemethanol-1-oxide To a solution of 1.5 g of (R)-6-Amino-α-[[(1,1-dimethyl-2-(1H-indol-3-yl)ethyl)amino]methyl]-3-pyridinemethanol in 20 ml of pyridine under nitrogen, acetic anhydride (10 ml) is added and the reaction mixture stirred at ambient temperature overnight. The mixture is then concentrated under reduced pressure. The crude acetylated product is treated with 0.9 g of m-chloroperbenzoic acid in 20 ml of CH₂Cl₂ for 4 hours at room temperature. The reaction mixture is concentrated once again and redissolved in 10 ml of methanol and treated with excess methanolic KOH solution at room temperature for 6 hours. The mixture is partially concentrated and then diluted with water and extracted repeatedly with CH₂Cl₂. The combined extracts is backwashed with saturated sodium chloride solution and dried with anhydrous magnesium sulfate. The solution is concentrated and the residue chromatographed on silica gel to give the (R)-6-Amino-α-[[(1,1-dimethyl-2-(1H-indol-3-yl)ethyl)amino]methyl]-3-pyridinemethanol-1-oxide.

EXAMPLE 19

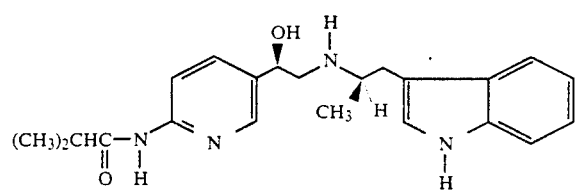

(R)-6-Isobutyramido-α-[[(1(R)-methyl-2-(1H-indol-3-yl)ethyl)amino]methyl]-3-pyridinemethanol A solution of 1.5 g of 2-isobutyramido-5-(bromoacetyl)pyridine and 1.0 g of (1(R)-methyl-2-(1H-indol-3-yl))ethyl amine in 50 ml of dry acetonitrile is stirred at room temperature for 30 minutes under nitrogen. The solution is made acidic with gaseous hydrochloric acid and then concentrated under reduced pressure. The residue is dissolved in methanol (35 ml) and cooled with an ice bath. To this cold solution excess sodium borohydride is added under nitrogen. The reaction mixture is stirred for one hour, partially concentrated and then diluted with water. The pH of the solution is adjusted to approximately 8–9 and then extracted repeatedly with CH₂Cl₂. The combined extracts are backwashed with saturated sodium chloride solution and dried with anhydrous magnesium sulfate. Concentration and chromatography on silica gel gives (R)-6-Isobutyramido-α-[[(1(R)-methyl-2-(1H-indol-3-yl)ethyl)amino]methyl]-3-pyridinemethanol and (S)-6-isobutramido-α-[[1(R)-methyl-2-(1H-indol-3-yl)ethyl)amino]methyl]-3-pyridinemethanol.

EXAMPLE 20

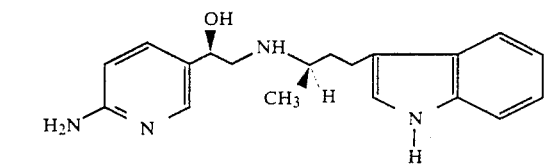

(R)-6-Amino-α-[[(1(R)-methyl-3-(1H-indol-3-yl)propyl)amino]methyl]-3-pyridinemethanol Dihydrochloride A solution of 16 g of 1-(1H-indol-3-yl)-3-butanone, 10.3 g of R(+)-1-phenylethylamine and 0.2 g of TsOH.H₂O in 80 ml of benzene is heated at reflux with water removal (Dean-Stark trap) for 24 hours. The reaction mixture is concentrated under reduced pressure and the residue redissolved in 80 ml of methanol. To this solution 8 g of Ra(Ni) catalyst is added and the mixture hydrogenated under positive hydrogen pressure for 32 hours. The reaction mixture is filtered through celite and the filtrate concentrated. The residue is chromatographed on silica gel to afford the (R,R,)-diastereomer. This material (6.2 g) is converted into its hydrochloride salt and dissolved in 50 ml of ethanol and hydrogenated over 1.6 g of 5% Pd(C) for 18 hours. The reaction mixture is then filtered and the filtrate concentrated under reduced pressure to dryness. The residue is chromatographed on silica gel to give 1(R)-methyl-3-(1H-indol-3-yl)propyl amine. This amine (650 mg) is condensed with 650 mg of (R)-2-(tetrazolo-[1,5-a]pyrid-6-yl)oxirane in 15 ml of absolute ethanol at reflux for 3 hours. The reaction mixture is concentrated under reduced pressure and the residue purified by chromatography on silica gel to give (R)-α-[[(1(R)-methyl-3-(1H-indol-3-yl)propyl)amino]methyl]tetrazolo[1,5-a]pyridine-6-methanol. This tetrazole (0.6 g) in 15 ml of methanol is treated with 0.6 g of SnCl$_2$·2H$_2$O and the reaction mixture heated at reflux for 18 hours. The reaction solution is partially concentrated under reduced pressure. This concentrated solution is added to a mixture of CH$_2$Cl$_2$ (20 ml) and 12 ml of 2N NaOH solution. The mixture is stirred for twenty minutes and then the layers are separated. The aqueous layer is further extracted with CH$_2$Cl$_2$. The combined organic extracts are backwashed with saturated sodium chloride solution and dried with anhydrous magnesium sulfate. The solution is concentrated and the residue chromatographed on silica gel to give the titled compound after conversion to its hydrochloride salt with ethanolic HCl.

EXAMPLE 21

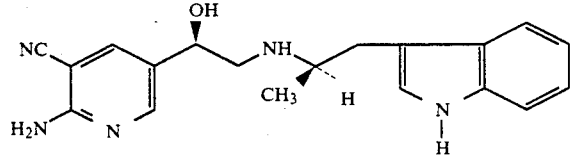

(R)-6-Amino-5-cyano-α-[[(1(R)-methyl-2-(1H-indol-3-yl)-ethyl)amino]methyl]-3-pyridinemethanol A solution of 0.5 g of 2-isobutyramido-3-cyano-5-(bromoacetyl)pyridine and 1.25 g of 1(R)-methyl-2-(1H-indol-3-yl)ethyl amine in 50 ml of dry acetonitrile under nitrogen is stirred for 30 minutes at room temperature. The reaction mixture is made acidic with gaseous hydrochloric acid and then diluted with ether. The solution is concentrated and the residue redissolved in methanol. The solution is cooled in an ice bath and treated slowly with sodium borohydride (0.4 g) for one hour. The pH of the solution is adjusted to approximately 6 with acetic acid and extracted with CH$_2$Cl$_2$. The combined organic extracts are backwashed with saturated sodium chloride solution, dried with anhydrous magnesium sulfate and concentrated under reduced pressure. The crude product is dissolved in 15 ml of methanol and treated with 0.7 g of KOH. The reaction mixture is heated at reflux for 2 hours and then partially concentrated. The solution is diluted with water and extracted with CH$_2$Cl$_2$. The combined extracts are backwashed with saturated sodium chloride solution and dried with anhydrous magnesium sulfate prior to concentration. The residue is chromatographed on silica gel to give (R)-6-Amino-5-cyano-α-[[1(R)-methyl-2-(1H-indol-3-yl)ethyl)amino]methyl]-3-pyridinemethanol and (S)-6-Amino-5-cyano-α-[[(1-(R)-methyl-2-(1H-indol-3-yl)ethyl)amino]methyl]-3-pyridinemethanol.

EXAMPLE 22

Additional derivatives can be prepared by reaction of the appropriate amine which may be prepared according to the literature references cited in the previous examples with (R)-2-(tetrazolo[1,5-a]pyrid-6-yl)oxirane and conversion of the resulting tetrazole 6 into the aminopyridine derivative 7 illustrated in Table 1.

TABLE I

Additional Products of Formula 7 in which the preferred structures of the heterocycle ethanol amine is:

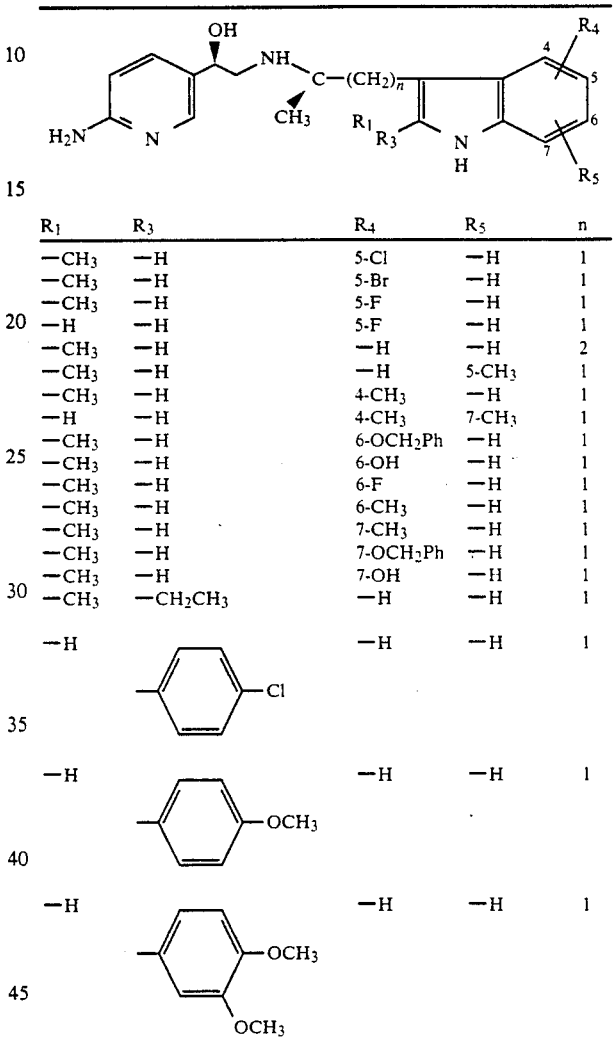

| R$_1$ | R$_3$ | R$_4$ | R$_5$ | n |
|---|---|---|---|---|
| —CH$_3$ | —H | 5-Cl | —H | 1 |
| —CH$_3$ | —H | 5-Br | —H | 1 |
| —CH$_3$ | —H | 5-F | —H | 1 |
| —H | —H | 5-F | —H | 1 |
| —CH$_3$ | —H | —H | —H | 2 |
| —CH$_3$ | —H | —H | 5-CH$_3$ | 1 |
| —CH$_3$ | —H | 4-CH$_3$ | —H | 1 |
| —H | —H | 4-CH$_3$ | 7-CH$_3$ | 1 |
| —CH$_3$ | —H | 6-OCH$_2$Ph | —H | 1 |
| —CH$_3$ | —H | 6-OH | —H | 1 |
| —CH$_3$ | —H | 6-F | —H | 1 |
| —CH$_3$ | —H | 6-CH$_3$ | —H | 1 |
| —CH$_3$ | —H | 7-CH$_3$ | —H | 1 |
| —CH$_3$ | —H | 7-OCH$_2$Ph | —H | 1 |
| —CH$_3$ | —H | 7-OH | —H | 1 |
| —CH$_3$ | —CH$_2$CH$_3$ | —H | —H | 1 |
| —H | (4-Cl-phenyl) | —H | —H | 1 |
| —H | (4-OCH$_3$-phenyl) | —H | —H | 1 |
| —H | (3,4-diOCH$_3$-phenyl) | —H | —H | 1 |

What is claimed is:

1. A compound having the formula

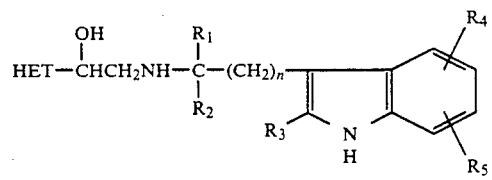

wherein Het is

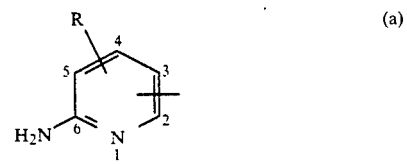

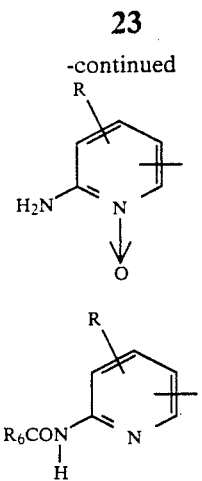

R is hydrogen, halogen or cyano;
R₆ is lower alkyl, phenyl, phenyl-lower alkyl;
R₁ and R₂ are independently selected from hydrogen or lower alkyl; R₃ is hydrogen, loweralkyl, phenyl, substituted phenyl, phenyl loweralkyl or substituted phenyl loweralkyl wherein the substituents are 1 to 3 of R₄ and R₅;
R₄ and R₅ are independently selected from hydrogen, loweralkyl, hydroxy, OR₇ or halogen;
R₇ is selected from lower alkyl or phenyl-lower alkyl; and n=1-3.

2. A compound of claim 1 wherein
R₁ and R₂ are independently selected from hydrogen or lower alkyl;
Het is selected form Structures (a), (c), or (d) and the ethanolamine moiety is attached to Het at the 3-position;
R₄ is hydrogen, halogen, hydroxy or OR₇;
R₅ is hydrogen;
R is hydrogen or halogen; R₇ is loweralkyl; and n is 1 or 2.

3. A compound of claim 1 wherein
Het is structure (a);
R₁ and R₂ are independently selected from hydrogen or methyl;
R₃ is hydrogen, methyl or ethyl;
R₄ and R₅ are hydrogen or - OR₇;
R₇ is hydrogen or methyl; R is hydrogen; and n is 1 or 2.

4. A compound of claim 1 wherein R₁ and R₂ are the same and wherein the compound is the R isomer.

5. A compound of claim 1 wherein R₁ and R₂ are different and wherein the compound is the R,R isomer.

6. A compound of claim 1 which is a hydrochloride, maleate or citrate salt thereof.

7. The compound of claim 1 which is (R)-6-amino-α-[[1(R)-methyl-2-(1H-indol-3-yl)ethyl)amino]methyl]-3-pyridinemethanol.

8. The compound of claim 1 which is (R)-6-amino-α-[[(1,1-dimethyl-2-(1H-indol-3-yl)ethyl)amino]methyl]-3-pyridinemethanol.

9. The compound of claim 1 which is (R)-6-amino-α-[[(1,1-dimethyl-2-(5-methoxy-1H-indol-3-yl)ethyl)amino]methyl]-3-pyridinemethanol.

10. The compound of claim 1 which is (R)-6-amino-α-[[(1,1-dimethyl-2-(5-hydroxy-1H-indol-3-yl))ethyl)amino]methyl]-3-pyridinemethanol.

11. The compound of claim 1 which is (R)-6-amino-α-[[(1,1-dimethyl-2-(5-benzyloxy-1H-indol-3-yl)ethyl)amino]methyl]-3-pyridinemethanol.

12. The compound of claim 1 which is (R)-6-amino-α-[[(1,1-dimethyl-2-(2-methyl-1H-indol-3-yl)ethyl)amino]methyl]-3-pyridinemethanol.

13. The compound of claim 1 which is (R)-6-amino-α-[[1(R)-methyl-2-(5-methoxy-1H-indol-3-yl)ethyl)amino]methyl]-3-pyridinemethanol.

14. The compound of claim 1 which is (R)-6-amino-α-[[(1(R)-methyl-2-(5-benzyloxy-1H-indol-3-yl)ethyl)amino]methyl]-3-pyridinemethanol.

15. The compound of claim 1 which is (R)-6-amino-α-[[(1(R)-methyl-2-(5-hydroxy-1H-indol-3-yl)ethyl)amino]methyl]-3-pyridinemethanol.

16. The compound of claim 1 which is (R)-6-amino-5-chloro-α-[[(1,1-dimethyl-2-(1H-indol-3-yl)ethyl)amino]methyl]-3-pyridinemethanol.

17. The compound of claim 1 which is (R)-6-amino-α-[[(1,1-dimethyl-2-(1H-indol-3-yl)ethyl)amino]methyl]-3-pyridinemethanol-1-oxide.

18. A method for the promotion of growth and increasing the feed efficiency of animals which comprises administering to such animals a pharmaceutically effective amount of a compound of claim 1.

19. A composition useful for promoting the growth and increasing the feed efficiency of animals which comprises compounding ingredients and an effective amount sufficient for growth promotion and increased feed efficiency of a compound of claim 1.

20. A method for promoting bronchodilation which comprises administering to patients in need of bronchodilation a pharmaceutically effective amount of a compound of claim 1.

21. A composition useful for promoting bronchodilation which comprises compounding ingredients and an effective amount sufficient for bronchodilation of a compound of claim 1.

22. A method for treating the symptoms of depression which comprises administering to a patient with depression a pharmaceutically effective amount of a compound of claim 1.

23. A composition useful for treating the symptoms of depression which comprises compounding ingredients and an effective amount sufficient for treating the symptoms of depression of a compound of claim 1.

24. A method for treating obesity which comprises administering to an obese patient a pharmaceutically effective amount of a compound of claim 1.

25. A composition useful for treating obesity which comprises compounding ingredients and an effective amount sufficient for treating obesity of a compound of claim 1.

* * * * *